United States Patent [19]

Ciago

[11] Patent Number: 4,805,239
[45] Date of Patent: Feb. 21, 1989

[54] COMBINATION TODDLER KNEE PADS AND/OR EAR MUFFS

[76] Inventor: Kim D. Ciago, 2375 E. 3rd St., Apt. 1-A, Brooklyn, N.Y. 11223

[21] Appl. No.: 146,491

[22] Filed: Jan. 21, 1988

[51] Int. Cl.⁴ .................. A41D 13/06; A41D 21/00
[52] U.S. Cl. ........................................... 2/24; 2/22; 2/62; 2/209; 2/209.1
[58] Field of Search .............. 2/22, 24, 62, 196, 209, 2/209.1

[56] References Cited

U.S. PATENT DOCUMENTS

| | | | |
|---|---|---|---|
| 213,764 | 4/1879 | Lighthall | 2/62 |
| 1,846,835 | 2/1932 | Bruckler | 2/24 |
| 1,896,561 | 2/1933 | Ruth | 2/24 |
| 1,969,527 | 8/1934 | Schnellbacher | 2/24 |
| 2,241,736 | 5/1941 | Reinemer | 2/209 |
| 2,626,394 | 1/1953 | Davis | 2/24 |
| 2,794,982 | 6/1957 | Kay | 2/24 |
| 3,508,544 | 4/1970 | Moore et al. | 2/24 |
| 4,120,052 | 10/1978 | Butler | 2/24 |
| 4,333,181 | 6/1982 | Corriero | 2/24 |
| 4,334,528 | 6/1982 | Gauvry | 2/24 |

Primary Examiner—Werner H. Schroeder
Assistant Examiner—Jeanette Chapman
Attorney, Agent, or Firm—Richard L. Miller

[57] ABSTRACT

This combination article is designed to be worn by toddlers to protect their knees and when desired they can also effectively function as ear muffs. Primarily, the article consists of an oval shaped pad with attached straps having mating hook and loop pile fasteners attached for adjustably securing the article to a toddler's knees or around the toddler's head. When secured to a toddler's head, a pair of the articles are secured together by the fasteners.

2 Claims, 1 Drawing Sheet

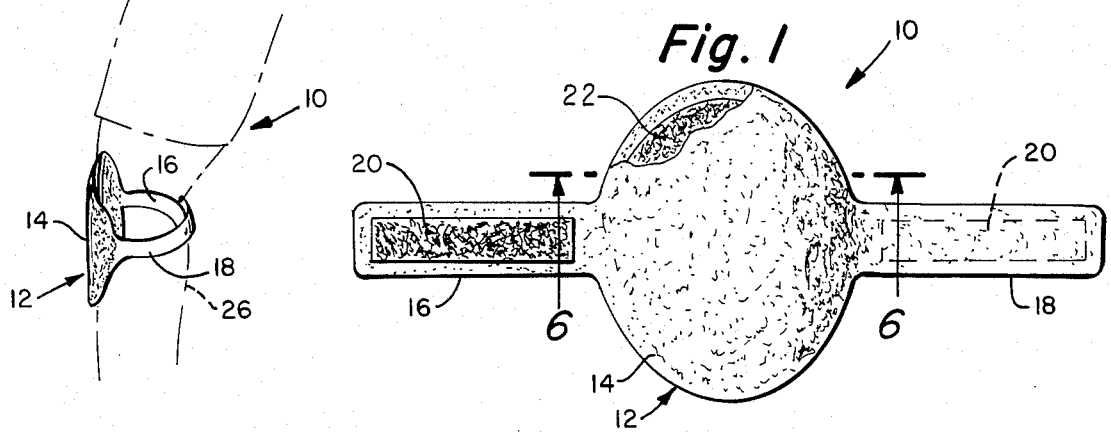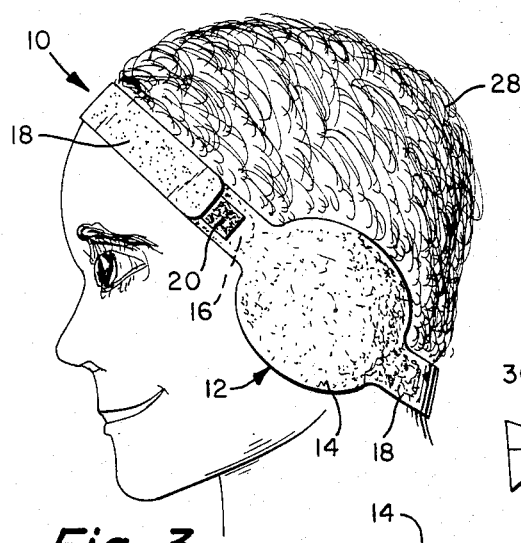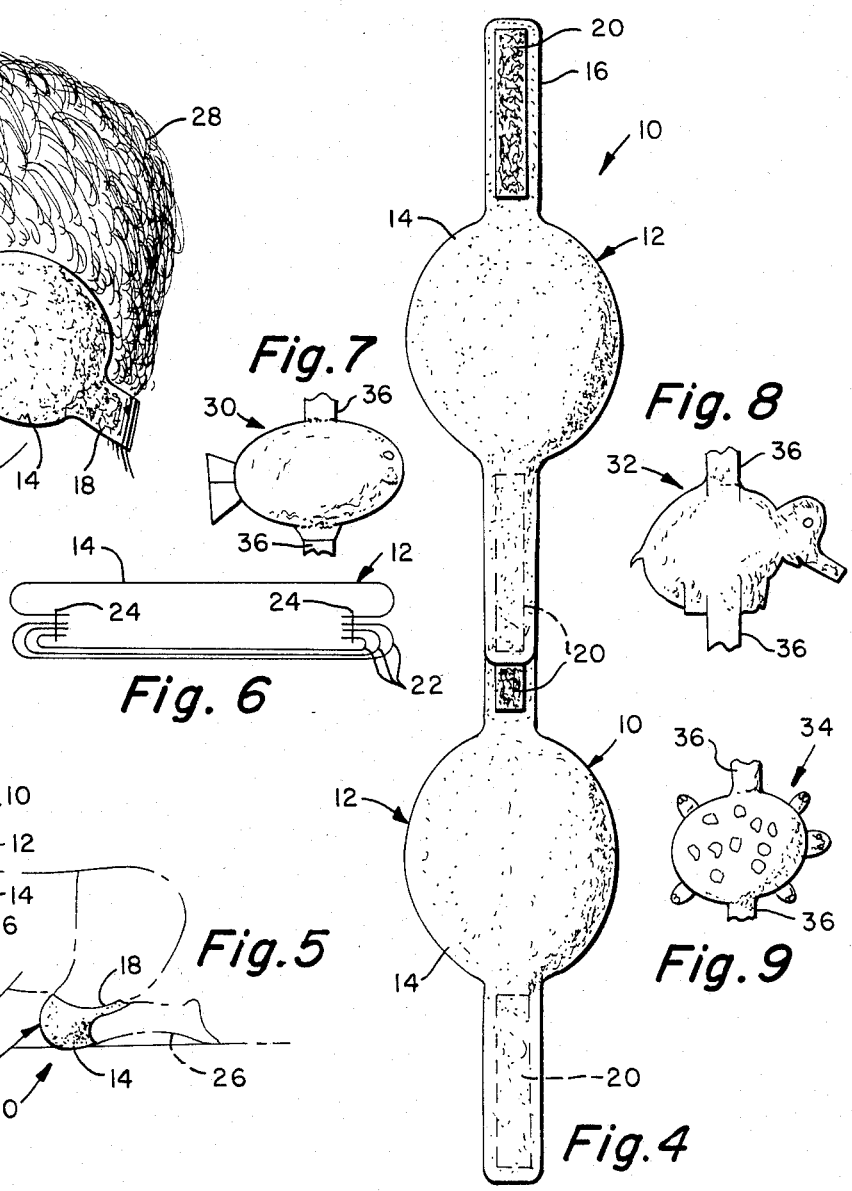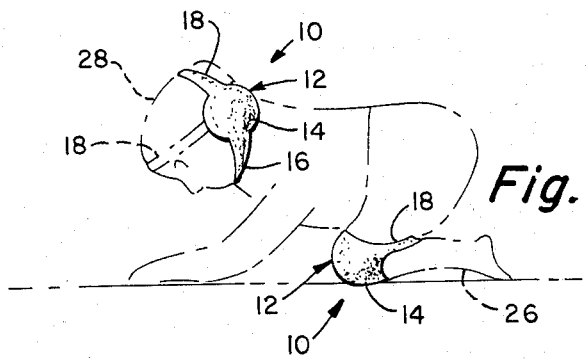

COMBINATION TODDLER KNEE PADS AND/OR EAR MUFFS

BACKGROUND OF THE INVENTION

The instant invention relates generally to articles for body protection, and more particularly, to combination toddler knee pads and/or ear muffs.

Numerous articles have been provided in the prior art that are adapted to protect toddlers and are worn by them. While these units may be suitable for the particular purpose to which they address, they would not be as suitable for the purpose of the present invention as hereafter described.

SUMMARY OF THE INVENTION

A primary object of the present invention is to provide combination toddler knee pads and/or ear muffs that will overcome the shortcomings of the prior art devices.

Another object is to provide combination toddler knee pads and/or ear muffs that will be of such design, as to be worn on a toddler's knees and can also be worn as cold weather protective ear muffs.

An additional object is to provide combination toddler knee pads and/or ear muffs that will be comfortable to wear and will have adjustable hook and loop pile fasteners, for fitting most toddlers.

A further object is to provide combination toddler knee pads and/or ear muffs that is simple and easy to use.

A still further object is to provide combination toddler knee pads and/or ear muffs that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only and that changes may be made in the specific construction illustrated and described within the scope of the appended claims.

BRIEF DESCRIPTION OF THE DRAWING FIGURES

The FIGS. in the drawings are briefly described as follows:

FIG. 1 is a perspective of the invention shown with parts broken away so as to illustrate the internal construction;

FIG. 2 is a perspective view of the invention shown in use as a knee/elbow pad on a toddler;

FIG. 3 is a partial perspective view shown employed as ear muffs;

FIG. 4 is a plan view showing the two units secured together, units secured to form the ear muffs of FIG. 3;

FIG. 5 is a side view of a toddler shown wearing the invention as both knee pads and ear muffs;

FIG. 6 is a diagrammatic cross sectional view taken along line 6—6 in FIG. 1 illustrating further internal construction thereof; and FIGS. 7, 8 & 9 illustrate typical embodiments of juvenile decorative FIGS. that may be integrally formed with the device.

DETAILED DESCRIPTION OF THE PREFERRED EMBODIMENTS

Turning now descriptively to the drawings, in which like reference characters denote like elements throughout the several views, a combination article 10 is shown to include a pad 12 composed on an outer pad panel 14 having a pair of oppositely opposed straps 16 and 18 integrally attached thereto. A pair of mating hook and loop pile fasteners 20 are fixedly secured to straps 16 and 18, one on opposite sides thereof, so as to facilitate fastening straps 16 and 18 together adjustably to a toddler.

A plurality of similar shaped pad panels 22 and fixedly secured to panel 14 by stitches 24, and article 10 is designed to fasten adjustably to a knee of a leg 26 of the toddler, or two of the articles 10 may be fastened together by their fasteners 20, so as to be employed as ear muffs as illustrated in FIGS. 3, 4 and 5 of the drawing.

It shall be noted that article 10 when employed as ear muffs, may be adjustably secured at the forehead of the head 28 of the toddler and the back of the neck, or optionally, the pair of secured together articles 10 may be secured at the top of the toddler's head 28 and under the toddler's chin, as illustrated in FIG. 5 and shows both applications (one in phantom).

In use, the pad 12 is placed on the knee of the leg 26 of the toddler, to be worn as protection of the knee, and the straps 16 and 18 are placed together and the fasteners 20 are pressed together to hold article 10 in place. When it is desired to remove article 10, the straps are simply pulled apart for disengagement of the fasteners 20.

When it is desired to employ article 10 as ear muffs, two of the articles 10 are secured together by their respective and mating pile fasteners 20, after which the endmost straps 20 are fastened together by the mating pile fasteners 20. In removal thereof, the same procedure is employed, as was above described.

Referring now to FIGS. 7, 8 and 9, modified articles 30, 32 and 34 are shown to include straps 36 and are of similar construction as was described of the main embodiment of the instant invention, however, article 30 is in the form of an air ship or fish, article 32 is in the form of an elephant, and article 34 is in the form of a turtle.

In use, articles 30, 32 and 34, function in the same manner as was heretofore described of article 10.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A combination toddler knee pad and ear muff article, comprising, an outer pad, a pair of straps secured to said outer pad, with mating loop and hook pile fasteners, for securing said article to a toddler's knee or head, wherein a single loop pile fastener is fixedly secured to one side of one of said straps and a single mating hook pile fastener is fixedly secured to one side of another of said straps, and when pressed together, said loop pile fastener and said hook pile fastener secures said article to said knee, and a pair of said articles are secured together for use as ear muffs, by mating engagement of a loop pile fastener of one of said articles and a hook pile fastener of another said article.

2. A combination as set forth in claim 1, wherein said pair of articles are engaged with ears of a toddler and secured about a toddler's head by a mating fastener of a strap of one article of said pair and a mating fastener of a strap of said another said article of said pair.

* * * * *